United States Patent [19]
Burtt, Jr. et al.

[11] Patent Number: 5,877,000
[45] Date of Patent: Mar. 2, 1999

[54] KERATINASE PRODUCED BY *BACILLUS LICHENIFORMIS*

[76] Inventors: Edward H. Burtt, Jr., 1898 Co. Rd. 156, Ashley, Ohio 43003; Jann M. Ichida, 265 Cottswold Dr., Delaware, Ohio 43015

[21] Appl. No.: 768,227

[22] Filed: Dec. 17, 1996

[51] Int. Cl.⁶ ..................................... C12N 9/56
[52] U.S. Cl. ................ 435/222; 435/220; 435/221; 435/68.1
[58] Field of Search .................. 435/222, 220, 435/221, 68.1

[56] References Cited

U.S. PATENT DOCUMENTS

| | | | |
|---|---|---|---|
| 2,988,487 | 6/1961 | Nickerson | 435/222 |
| 2,988,488 | 6/1961 | Robison | 435/68.1 |
| 3,751,222 | 8/1973 | Gobert | 252/95 |
| 5,171,682 | 12/1992 | Shih | 435/222 |

OTHER PUBLICATIONS

El–Shora et al., J. Environ. Sci. (Mansoura, Egypt) (1993), 6, 89–103.

Molyneaux, G. S., Aust. J. Biol. Sci. 274 (1959).

*Primary Examiner*—Irene Marx
*Attorney, Agent, or Firm*—Isaac A. Angres

[57] ABSTRACT

*Bacillus licheniformis* O.W.U. 138B and 88B and other bacterial strains capable of degrading feathers isolated from wild birds, are disclosed. The strains and the keratinases produced by these strains are useful for degrading waste feathers produced by commercial poultry processing; producing animal feed, fertilizer, or natural gas from poultry waste; and cleaning of certain fabrics.

4 Claims, No Drawings

KERATINASE PRODUCED BY *BACILLUS LICHENIFORMIS*

FIELD OF THE INVENTION

The present invention generally relates to bacterial strains useful for degrading keratin. More particularly, the invention relates to isolating from wild birds bacterial strains capable of degrading feathers. The invention also relates to the keratin-degrading enzymes produced by these bacterial strains. Another aspect of the invention is processes in which the bacterial strains and enzymes can be used, such as the disposal of waste feathers and dead birds; the production of animal feed, natural gas, or fertilizer from poultry waste; and the cleaning of fabrics.

BACKGROUND OF THE INVENTION

Keratins are a major class of structural proteins that are highly resistant to biological degradation. Common enzymes which break down protein, such as trypsin, do not affect keratin. Keratins are insoluble in water. Keratins, like other proteins, are made of a long string of various amino acids, which fold into a final 3-dimensional form. Alpha helix and beta sheet are common parts of such a 3-dimensional form. Long, thin biological structures often contain alpha helixes, while flat structures are often built from beta sheets. Some keratins are rich in alpha helix structures, while others are mostly beta sheet. These two major types of keratin are known as alpha-keratin and beta-keratin. Wool and hair are largely composed of alpha-keratin. Feathers are largely composed of beta-keratin.

The poultry processing industry produces huge quantities of turkey and chicken feathers as a by-product. These feathers constitute a sizable waste disposal problem. Several different approaches have been used for disposing of feather waste, including landfilling, burning, natural gas production, and treatment for animal feed. Most feather waste in the United States is landfilled or burned, which involves expense and can cause contamination of air, soil and water.

Natural gas production from waste materials is rarely used in the U.S., due to the low price of U.S. natural gas and the availability of land for landfilling. Thermophilic anaerobic poultry waste digestors are known which can produce significant amounts of natural gas from poultry manure and other waste. Bacteria are combined in these digesters with the poultry waste, fermented, and the natural gas produced is collected. The effluent remaining after fermentation can be used as animal feed or fertilizer.

Animal feed typically includes a carbohydrate source and a protein source. The protein source provides needed amino acids to the animal. Common protein sources used in animal feed include soy meal; fish meal; blood meal; meat or poultry by-products; and meat and poultry meal. These protein sources are generally expensive. Feather waste is high in protein and very inexpensive, but cannot be used directly in animal feed, as it is difficult for animals to digest. A small percentage of feather waste is steamed, chemically treated, ground, or some combination of these to form feather meal. Feather meal is used as a dietary protein supplement for animals. Typical treatments to form feather meal are expensive. These treatments also tend to destroy some amino acids, such as heat-sensitive amino acids when steam treatment is used. This lowers the quality of the protein in the feed. Due to these problems, feather meal is not extensively used in feed, despite the expense of other sources of dietary protein.

Bacterial strains are known which are capable of degrading feathers. These bacterial strains produce enzymes which selectively degrade the beta-keratin found in feathers. These enzymes make it possible for the bacteria to obtain carbon, sulfur, and energy for their growth and maintenance from the degradation of beta-keratin. An enzyme capable of degrading protein is known as a protease, and is described as having proteolytic activity. An enzyme which degrades keratin is a keratinase, while a beta-keratinase is an enzyme capable of degrading beta-keratin. An enzyme which degrades keratin can also be described as having keratinolytic activity. The same enzyme can be referred to as a protease, a keratinase, and a beta-keratinase if it has all three properties.

Prior feather-degrading bacterial strains, such as *Bacillus licheniformis* PWD-1 (ATCC 53757), have been isolated from chicken waste and poultry waste digesters. See generally Williams, C. M. et al, Isolation, Identification, and Characterization of a Feather-Degrading Bacterium, *Applied and Environmental Microbiology*, Vol. 56, No. 6, June 1990, pp. 1509–1515. Specific primers, probes, and polymerase chain reaction (PCR) techniques for the keratinase gene of *B. licheniformis* PWD-1 are known. Keratinolytic microorganisms have been found in soil and agricultural compost. U.S. Pat. Nos. 5,063,161 and 4,959,311 describe methods of degrading keratinaceous material and bacteria useful for such degradation. U.S. Pat. No. 5,171,682 describes a purified *B. licheniformis* PWD-1 keratinase capable of degrading feathers. U.S. Pat. No. 5,186,961 describes a method and composition for maintaining animals on a keratin-containing diet. U.S. Pat. No. 4,908,220 describes a hydrolyzed feather feed ingredient (feather-lysate) and animal feeds containing feather-lysate.

Large numbers of dead, unsaleable birds are another waste product produced by commercial poultry processing. Since the feathers are resistant to degradation, the feathers often remain after the soft parts of a dead bird have decomposed. Other wastes from poultry processing, such as poultry manure, often contain significant amounts of difficult-to-degrade feathers. The feathers in these waste products make disposal more difficult and expensive.

Proteins make up many common stains that are found on clothing. When the proteins involved are insoluble in water, the stain is often difficult to remove. Blood stains are an example. Addition of enzymes capable of degrading proteins to detergents for cleaning clothes is well known in the art, U.S. Pat. No. 5,079,154. Since keratin is a protein which is insoluble in water, enzymes with keratin-degrading activity are known to be effective detergent additives.

*B. licheniformis* is a rod-shaped, endospore-forming bacteria. The rods are often in chains. Colonies on agar are opaque with dull to rough surface. Wrinkled outgrowths are common. The colonies are usually attached strongly to the agar, and mounds and lobes consisting largely of slime often accumulate on the colony, especially on glucose agar or glutamate-glyceral agar. Glutamyl polypeptide is formed as an extracellular amorphous slime. Levan is produced extracellularly from sucrose and raffinose. Red pigment is formed by many strains on carbohydrate media containing sufficient iron. Aged cultures may become brown. Freshly isolated strains grow with ammonia as the sole source of nitrogen in the absence of growth factors. Spores are known to occur in soil. Many spores survive severe heat treatment. Refer generally to *Bergey's Manual of Systematic Bacteriology*, Vol. 2, Section 13, P.H.A. Sneath, ed., Williams & Wilkins, L.A.

SUMMARY OF THE INVENTION

The present invention includes three methods of screening a wild bird for the presence of feather-degrading bacteria.

The first method involves as a first step capturing a wild bird and rubbing the feathers of the bird with a sterile applicator dipped in a sterile saline solution. Next, the applicator is placed in a nutrient broth of sodium chloride content ranging from 7.0% to 8.0% weight/volume and a pH ranging from 7.0 to 7.7. Preferably the nutrient broth contains 7.5% weight/volume sodium chloride and is of a pH ranging from 7.5 to 7.7. Next the broth is incubated at a temperature between 45° C. and 60° C. for a period of 2 to 14 days. Preferably the broth is incubated for 7 days at a temperature ranging from 50° C. to 55° C. Next, any surviving bacteria are grown on trypticase soy agar until colonies are formed, and bacteria from an individual colony are transferred to a physiologically balanced solution containing feather. The solution is incubated at a temperature between 35° C. and 60° C. for a period of 1 to 28 days. Solutions in which the feather is not degraded are discarded, while solutions in which the feather is degraded are retained.

The second method of screening a wild bird for the presence of feather-degrading bacteria involves as a first step, capturing a wild bird and rubbing the feathers of the bird with a sterile applicator. Next the sterile applicator is rubbed across an agar plate containing salt, vitamin, yeast extract, and keratin. The plate is then incubated between 35° C. and 60° C.; and any bacterial colonies on the agar plate which show growth are retained.

The third method of screening a wild bird for the presence of feather-degrading bacteria is by the polymerase chain reaction (PCR). Genes coding for the production of keratinase are present in the DNA of two bacterial strains isolated from wild birds, *Bacillus licheniformis* O.W.U. 138B and *B. licheniformis* O.W.U. 88B. Probes developed from one or more of these genes are used to detect keratinase-producing bacteria.

Part of the present invention is the two bacterial strains isolated from wild birds. These strains are *Bacillus licheniformis* O.W.U. 138B, having the identifying characteristics of ATCC 55768, and *Bacillus licheniformis* O.W.U. 88B, having the identifying characteristics of ATCC 55769. Other aspects of the invention are a substantially pure culture of one or both of these strains, capable of degrading feathers; and a crude, cell-free extract of these strains.

The invention includes a method of degrading feathers using the 138B and 88B strains. The first step in this process is combining keratin with one or both of these strains. The enzyme produced by the bacteria is then allowed to degrade the keratin. The keratin may be in the form of feathers, dead birds, poultry waste, or combinations of these. The keratin and the bacteria may be combined with poultry manure and water to degrade into compost. There may be a further step of treating the feathers to facilitate enzymatic degradation prior to the step of combining the feathers with the bacterial strain. This treatment may consist of steam treatment, chemical treatment, grinding, hammer-milling, or combinations of these. There may be a step of disposing of degraded feathers by landfilling, applying to soil, mixing with soil, covering with soil, or using the degraded feathers as fertilizer for agricultural purposes. The degradation may be used to produce a dietary protein product suitable for use in animal feed. The degradation may take place after the feathers are landfilled or otherwise disposed of. There may be a further step of collecting natural gas produced by the degradation.

Keratinases produced by *B. licheniformis* strains O.W.U. 138B and 88B are also an object of the invention. The keratinases may be combined with feathers to enhance the digestibility of the feathers in an animal's digestive tract. The keratinases may be dispersed in a suitable cleaning medium in a concentration sufficient to remove protein-based stains from a fabric without significant damage to the fabric. The fabric may be wool or silk.

Also part of the invention is a method of degrading keratin by combining the keratin with the keratinases produced by *B. licheniformis* strains O.W.U. 138B and 88B and allowing the keratinases to degrade the keratin. The keratinases may be combined with waste feathers before disposing of the feathers by landfilling or other means such as applying to the soil, mixing with soil, covering with soil, and fertilizing for agricultural purposes. In this case the degradation of the keratin takes place after the step of disposing of the feathers.

The present invention includes a method for preparing a keratinase. This method includes the steps of combining *B. licheniformis* strains O.W.U. 138B or 88B with a medium, allowing the strain to grow for a time sufficient to produce a large quantity of a keratinase, and purifying the keratinase. The purification step may include tangential-flow filtration to remove crude cell mass and large proteins; purification by ion-exchange chromatography; purification by size-exclusion chromatography; and various ultrafiltration steps to concentrate the enzyme.

Also part of the invention is a method for preparing a keratinase using genetic engineering. The first step of this method is inserting into a suitable host cell using a suitable vector a DNA sequence coding for the production of keratinase in *B. licheniformis* strains O.W.U. 138B or 88B. The next step is screening for keratin-degrading ability in a transformed cell. Once the transformed cell is found, keratinase is produced by allowing the transformed cell to grow in a medium for a time sufficient to produce a large quantity of keratinase. Lastly the keratinase is purified.

DESCRIPTION OF THE PREFERRED EMBODIMENTS

The present invention consists of bacterial strains capable of degrading feathers, isolated from wild birds; the keratinases produced by these strains; processes for using the strains and keratinases; and products produced by these processes.

Feathers do not normally accumulate in the wild, which may be due to feather-degrading bacterial strains naturally present on wild birds. One of the reasons for the regular molting of old feathers may be to prevent the accumulation of such bacteria before serious damage to feathers occurs. Feather color affects the degradation of feathers by bacteria, with darkly colored feathers degrading more slowly than white feathers. Bacterial degradation may be a factor in the evolution of feather color.

The applicants sampled 1184 wild birds belonging to 73 species. Wild birds were captured in the field in mist nets or Potter traps. Birds were captured in several locations in the Delaware Wildlife Refuge, at the Bohannan Forest Preserve and Kraus Wilderness Preserve of Ohio Wesleyan University, at Manomet Observatory for Conservation Sciences and at the home of one of the applicants. Feather-degrading bacteria were collected from the birds and tested for feather degrading ability.

Feather-degrading bacteria from the captured wild birds were collected by rubbing the feathers gently with sterile dacron-tipped applicators (Puritan) that had been dipped in sterile, normal (0.85% NaCl) saline. A separate swab was used for each location sampled on a bird. Generally the locations sampled for each bird were the feathers of the back, the feathers of the stomach, and the upper surface of the tail feathers. The exposed swabs were stored in sterile envelopes for transport to the laboratory. The swabs were then placed in alkaline salts nutrient broth in test tubes and incubated for 7 days at 50° C. Preferably the nutrient broth pH was 7.5 and its salinity was 7.5% NaCl. This new and unusual alkaline nutrient broth was specially developed to select for salt-tolerant, thermophilic species of *Bacillus*.

Bacterial growth was indicated by turbidity of the nutrient broth. If the broth remained clear, bacteria were considered absent and the culture was discarded. Surviving samples were then streaked across a sterile plate of trypticase soy agar and incubated for 24 hours at 35° C. This procedure enabled the morphology of the bacterial colonies to be checked to ensure only a single bacterial species was involved. Isolated colonies were also provided from which representative colonies could be selected. The selected samples were transferred using sterile loops to nutrient agar slants, such as trypticase soy agar slants. The slants were incubated for 24 hours at 35° C. If necessary the cultures were then refrigerated at 4° C. before being tested for feather degradation ability. To confirm species identification, some samples were sent to an independent laboratory.

To test for feather degradation ability, the bacteria were transferred to a physiologically balanced solution in which a feather was the primary source of carbon, nitrogen, and energy. If the feather was degraded, the sample was labeled and saved. A standard procedure was used to quantify the rate of feather degradation by various bacterial strains, to compare the strains with one another.

The first step in the standard feather-degradation test procedure was removing 1 cm from the end of a white, secondary feather cut from a leghorn chicken (the distal tip) and discarding this portion. The next step was removing the next 2 cm from the same feather, and weighing this portion on a Mettler electronic balance accurate to 0.001 g. This feather portion was submerged in 10 mL of physiologically balanced solution in a test tube. The adjacent 2 cm of the feather was placed in a different test tube. The next step was sterilizing the test tube in an autoclave for 15 minutes at 121° C. and 17 lbs. pressure. If necessary, the bacterial isolates to be tested were removed from cold storage. Fresh trypticase soy agar cultures were inoculated with the bacteria as needed, and incubated for 24 hours. A loopful of the bacterial culture to be tested was suspended in sterile saline solution. The turbidity of the saline-bacterial suspension was adjusted to the desired cell concentration. Preferably this was 0.5 on the MacFarland scale (150,000 cells per mL), but $10^7$ cells per mL was also used. After cooling, the autoclaved test tube of physiologically balanced solution containing a feather portion was inoculated with 0.2 mL of the saline-bacterial suspension being tested. The tube was placed in a rack on a shaker that oscillated at 175 rpm and incubated at 50° C. The tube was then checked daily for turbidity of the solution and the condition of the feather. At the conclusion of the degradation period, the contents of the test tube were filtered through a membrane filter and the residue weighed. The feather was considered degraded when only pieces 0.5 $mm^2$ or smaller remained.

Bacteria were also collected from nestlings and from bird nests before, during and after eggs were laid in the nests. Nest material was sampled by collecting a small representative sample of nest material in a sterile plastic Whirl-Pak bag, blending 0.1 g of the material in 99 mL of physiological saline with a phosphate buffer, transferring 1 mL of this suspension to another 99 mL of saline, and transferring 0.1 mL or 0.5 mL of this suspension into petri dishes. Warm sterilized trypticase soy agar was poured into the dish and mixed with the suspension. This mixture was allowed to gel and incubated at 35° C. Colonies of bacteria and fungi were counted and characterized in the standard manner after 24 hours and again after 7 days. Colonies of bacteria were tested for feather degrading ability in the usual way. Bacteria were collected from nestlings and from nest boxes by rubbing with sterile dacron swabs in a manner similar to that used for adult birds.

In some cases, the exposed swab was streaked onto trypticase soy agar, manitol salts agar, eosin methylene blue agar, yeast malt agar, actinomycetes isolation agar, or other culture media, before incubating the swab itself in the nutrient broth. Contact plates of these culture media were also pressed directly on the feathers of the captured wild birds in some cases. These media were generally incubated at 35° C. and colonies were counted and characterized at 24 hours and again at seven days. This procedure allowed for identification and collection of various types of bacteria and fungi in addition to feather-degrading bacteria.

Due to the many steps involved in the above process for collecting feather-degrading bacteria from wild birds and testing for feather degrading ability, a single-step assay was also developed using a keratin/salt agar. A swab used to collect bacteria from a bird was rubbed across an agar plate containing salt, vitamin, yeast extract, and keratin. The plate was incubated at 50° C. and checked for bacterial colonies. Bacterial colonies showing growth were retained.

The invention also includes an assay based on the polymerase chain reaction (PCR) to detect and identify *B. licheniformis* on the feathers of birds. DNA isolated from *B. licheniformis* strains 138B and 88B can be used to develop a probe for detection of keratinase-producing bacteria.

This will enable rapid detection and identification of feather-degrading bacteria. Feather-degrading bacteria were found on 66 individual birds belonging to 25 species. 17 of the bacterial samples were identified by an independent, commercial reference laboratory, confirming that most of the feather-degrading bacteria were *Bacillus licheniformis*. Most of the isolated strains of *B. licheniformis* were able to degrade feathers to some extent. Also among the bacterial samples were three specimens of *B. pumelis*, one specimen of *B. macerans* and one specimen of *B. subtilis*, which showed a limited ability to degrade feathers. All four of these species are closely related members of *Bacillus* phenotype group II. *Streptomyces fradiae*, possibly a feather-degrading species was seldom found among the samples. Keratinolytic fungi are also known to exist on the feathers of birds, but were not found among the samples. Based on these results, the invention preferably involves feather-degrading strains of *B. licheniformis*.

About 7–8% of wild birds sampled were found to carry feather-degrading *B. licheniformis* on their feathers. The number of birds carrying feather-degrading bacteria was found to vary from month to month throughout the year, possibly as a result of the molting cycle. Feather-degrading *B. licheniformis* was most common in the winter. Feather degrading strains were somewhat less common in late fall, spring and early summer, and absent from late August to late October. Most of the birds sampled were captured in habitats of old fields and low brush, rather than forest or marshland. Bird species that foraged on the ground for food generally had a high incidence of feather-degrading bacteria. *B. licheniformis* was most commonly found on the stomachs of birds. This may be due to contact with the soil. *B. licheniformis* forms spores which enable it to survive long periods of unfavorable conditions. These spores can also be carried in the air.

Of the large number of samples that were taken from wild birds, B. licheniformis strains 138B and 88B were the most effective in degrading feathers. Strain 138B was taken from a willow flycatcher. Strain 88B was taken from a yellow warbler. Strain 138B is also known to degrade samples of chicken toenails, beaks and skin.

Any suitable liquid growth medium may be used for the growth in quantity of B. licheniformis strains 138B and 88B. Preferably the growth medium includes feathers.

B. licheniformis strain 138B was found to be negative for adonitol, dulcitol, raffinose, tryptone 1% (indole), urease activity, KCN, ramnose, lipid hydrolysis, oxidase activity, and xylose. Strain 138B was found to be positive for azide (0.05%), candle jar, casein hydrolysis, catalase activity, DNA, Simmons citrate, and nitrate. Acid, but not gas, was produced from fructose, galactose, glucose, maltose, mannitol, mannose, saccharose, sucrose, arabinose, inulin, and lactose by strain 138B. There was weak production of acid from sorbitol by strain 138B. Strain 138B was found to grow best at a NaCl concentration of between 2 and 4% and at temperatures between 35° and 50° C.

Bacillus licheniformis O.W.U. 138B was deposited with the American Type Culture Collection in accordance with the Budapest Treaty on May 10, 1996, and has been assigned ATCC Accesion No. 55768.

Bacillus licheniformis O.W.U. 88B was deposited with the American Type Culture Collection in accordance with the Budapest Treaty on May 10, 1996, and has been assigned ATCC Accesion No. 55769.

Any suitable method for producing a crude, cell-free extract or a substantially pure keratinase from B. licheniformis strains 138B or 88B may be used. The bacterial cells may be lysed, or the cells may be separated from the proteins produced by them. Refer generally to Shih, J. et al., Purification and Characterization of a Keratinase from a Feather-Degrading Bacillus licheniformis Strain, *Applied and Environmental Microbiology* 58: 3271–3275 (1992). SDS polyacrylamide gel electrophoresis (SDS-PAGE) suggests a molecular weight of approximately 40 kDa for the keratinase produced by strain 138B. Isoelectric focusing indicates a pI of 5.5 for this keratinase. The keratinase produced by strain 138B is a serine protease; it exhibits keratinase activity and general proteolytic activity. PWD-1, the other feather-degrading bacterium, produces a keratinase with a molecular weight of 33 kDa and a pI of 7.25.

A standard qualitative scale of feather condition was also developed to aid in comparing degradation. This scale was a modification of Butt's. Feathers are composed of a rachis or shaft, with barbs attached on each side of the rachis. Adjacent barbs are normally hooked together. Feather condition was rated on a scale of 0.0 to 3.0. The ratings are described as follows. 0.0: the feather was completely degraded, with only minute particles of the rachis visible in the solution. 0.5: all barbs were detached from the rachis and in pieces; the rachis was present, but in pieces. 1.0: most or all of the barbs were detached from the rachis. 1.5: the barbs were separated from each other, with half of the barbs detached from the rachis. 2.0: the barbs were slightly separated, with a few barbs detached from the rachis. 2.5: many barbs were separated from one another, with pronounced fraying at edges. 3.0: the feather was intact, with ¾ or more of the barbs attached to one another. 3.0 was the usual condition after autoclaving the feather, before any degradation. When one segment of a feather was more degraded than the other, the sample was given an intermediate rating that best described the overall picture.

The most active bacterial strains were found to completely degrade a feather in 3 days. The least active strains were found to require 14 or more days.

Experiments were carried out to establish the pH and temperature under which B. licheniformis degraded feathers. Optimal conditions were found to be 50° C. at pH 7.5. Complete degradation also occurred at 35° C. and pH 7.5, but the process took about twice as long. At 50° C. and pH 5.5 degradation of feathers did not occur.

Bacillus licheniformis strains O.W.U. 138B and O.W.U. 88B were deposited with the American Type Culture Collection in accordance with the Budapest Treaty on May 15, 1996. 138B has been assigned ATCC Accession No. 55768 and 88B has been assigned ATCC Accession No. 55769.

The structure of the keratinases of the present invention (strains of B. licheniformis isolated from wild birds) is not known. The mechanism of keratin degradation in these strains is also not known. It is not known whether differences in levels of feather-degrading ability are due to different enzyme structures, different levels of the same enzyme, or the presence of inhibitors.

The present invention includes DNA sequences which code for the production of feather-degrading B. licheniformis O.W.U. 138B and O.W.U. 88B beta-keratinases. These DNA sequences may be inserted into suitable host cells using suitable vectors using known techniques. Host cells may be prokaryotic or eukaryotic. Suitable vectors may include bacteriophages, plasmids, and viruses. Transformed host cells may be screened for by growing on an agar medium containing beta-keratin.

The bacterial strains and keratinases of the invention may be used as a protein source for animal feed in various ways. The feathers may be pre-digested using B. licheniformis strains O.W.U. 138B or O.W.U. 88B, and the resulting feather meal may be included in feed. Alternatively, beta-keratinase produced by B. licheniformis strains O.W.U. 138B and O.W.U. 88B may be added to animal feed in combination with feathers. In this case the enzymatic degradation of the feathers occurs within the digestive tract of the animal. The feathers may be the sole protein source in the animal feed or there may be an additional protein source. The feathers may be ground, steam-treated, or otherwise prepared before adding to the feed to ensure adequate degradation by the enzyme. The animals to be fed may be poultry or any domestic animal.

The keratinases of the invention may also be useful in degrading collagen, elastin, and other structural biological materials and peptides containing significant amounts of beta-sheet structure. The enzymes may be useful in commercial composting and other industrial and household applications involving degradation of such proteins.

An additional waste disposal problem of commercial poultry farms is that of disposing of dead birds. Many such birds are buried or burned. Due to the natural resistance of keratin to biological degradation, feathers often remain after the soft tissues of the birds have decomposed. Collagen and elastin are found in birds, and are also somewhat resistant to degradation. Collagen and elastin also tend to remain after the decomposition of soft tissues. Other wastes from poultry processing, such as poultry manure, often contain significant amounts of difficult-to-degrade feathers.

The present invention includes a method for degrading the keratin found in dead birds and other poultry waste by composting. A bacterial strain of B. licheniformis 138B or 88B is added to a composter, preferably along with poultry manure, straw, water, and dead chickens. The composter preferably measures 3'×3'×3', is made from ordinary lumber, and rests on a concrete pad. Two or three such composters can handle the normal mortality of a 25,000 chicken flock. The feather-degrading bacteria hasten the degradation of the feathers. Strains 138B and 88B may also hasten the decomposition of collagen and elastin, as *B. licheniformis* PWD-1 is known to partially degrade these materials.

The present invention also includes the use of beta-keratinases produced by *B. licheniformis* strains 138B and 88B as an enzymatic additive for clothing cleaning products. Animal hair is made primarily of alpha-keratin, while feathers are primarily beta-keratin. Wool and some other fibers commonly used in clothing are therefore mostly alpha-keratin. The beta-keratinases of the invention have been found to selectively degrade beta-keratin, while leaving alpha-keratin largely intact. Beta-keratinases can therefore be particularly useful as enzymatic cleaners for woolen products and some other clothing fabrics. While the addition of protein-degrading enzymes to cleaning products is known, clothing fibers which are made of proteins tend to be degraded by the same enzymes. In particular, many natural fibers, especially wool and silk, are difficult to clean completely since cleaning products capable of removing difficult stains such as blood and vegetable dyes also attack the fabric. This can lead to a weakening of the fabric. If an enzyme can specifically degrade the material of the stain, while leaving the stained material intact, this can produce a cleaner that is mild but still very effective. Enzymatic cleaning products including beta-keratinases are effective in removing protein stains from clothing fibers composed of alpha-keratin but are less likely than other proteases to weaken the fabric. Silk is composed of keratin (but not of alpha-keratin), and the keratinases of the invention may be useful as enzymatic cleaners for silk as well. Beta-keratinases may also be useful in hard surface cleaners and personal care products as well as laundry detergents.

The invention will be more fully described in conjunction with the following specific examples which are not to be construed as limiting the scope of the invention.

EXAMPLE 1

A wild bird is captured and the feathers of the bird are rubbed with a sterile applicator dipped in a sterile saline solution. Next, the applicator is placed in a nutrient broth of sodium chloride content ranging from 7.0% to 8.0% weight/volume and a pH ranging from 7.0 to 7.7. Preferably the nutrient broth contains 7.5% weight/volume sodium chloride and is of a pH ranging from 7.5 to 7.7. Next the broth is incubated at a temperature between 45° C. and 60° C. for a period of 2 to 14 days. Preferably the broth is incubated for 7 days at a temperature ranging from 50° C. to 55° C. Next, any surviving bacteria are grown on trypticase soy agar until colonies are formed, and bacteria from an individual colony are transferred to a physiologically balanced solution containing feather. The solution is incubated at a temperature between 35° C. and 60° C. for a period of 1 to 28 days. Solutions in which the feather is not degraded are discarded, while solutions in which the feather is degraded are retained.

EXAMPLE 2

The nutrient broth to select for thermophilic, salt-tolerant strains of *B. licheniformis* is a modified Difco-Bacto nutrient broth. The broth contains 3 g/L of beef extract, 5 g/L of peptone, 75 g/L of sodium chloride, with 2N sodium hydroxide added to raise the pH to 7.5–7.7 before sterilizing the broth. A swab from each location sampled on a bird is incubated in the nutrient broth for 7 days at 50° C.

EXAMPLE 3

Media for a starter culture for growth in quantity of strain 138B and for growth in quantity of 138B are detailed as follows.

The medium used as a starter culture for growth in quantity of *B. licheniformis* strain 138B is 5 made from the following solutions: 10 g $NH_4Cl$ in 200 mL of water; 10 g NaCl in 200 mL of water; 2 g $MgCl-6$ $H_2O$ in 200 mL of water; 6 g $K_2HPO_4$ in 200 mL of water; and 8 g $KH_2PO_4$ in 200 mL of water. Water used in the solutions is deionized. 10 mL of each of these solutions is combined with 950 mL of deionized water, the pH is adjusted to 7.5, and 10 g of commercial USB keratin is dissolved in the solution. The starter medium is autoclaved, 100 mL of the medium is inoculated with strain 138B, and the medium is incubated at 50° C. for 24 hours with shaking.

The medium used for growth in quantity of *B. licheniformis* strain 138B is made from the following solutions: 10 g $NH_4Cl$ in 200 mL of water; 10 g NaCl in 200 mL of water; 2 g $MgCl-6$ $H_2O$ in 200 mL of water; 10 g KCl in 200 mL of water; 6.88 g piperazine and 1692 mL of 6M HCl in 4 L of water (20 mM piperazine buffer of pH 6.0). Water used in the solutions is double distilled. 10 mL of each of these solutions is combined with 950 mL of deionized water. The pH is adjusted to 6.0 using 1M HCl, and 0.1 g of yeast extract is added. The growth medium is autoclaved, cooled to 55° C., and the incubated starter culture above is added. About 8 g of clean feathers is added and the solution is grown in a 1 L fermenter for 3 days.

EXAMPLE 4

The beta-keratinase produced by strain 138B is isolated and purified by the following steps. Bacteria of strain 138B are grown in quantity in mechanical fermenters. 0.45 micron tangential-flow filtration of the culture is performed to remove crude cell mass and large proteins. 10,000 Dalton tangential-flow ultrafiltration of filtrate is performed to remove proteins smaller than 10 kDa and reduce the volume. The retentate is purified using ion-exchange chromatography and active samples are concentrated using Minitan ultrafiltration. The retentate from this process is purified using size-exclusion chromatography and the active samples are again concentrated using Minitan ultrafiltration. An Amicon Stirred Cell unit with a 10 KDA Ultrafiltration membrane is used to reduce the volume and concentrate the enzyme sample. Ion-exchange chromatography is performed on a DEAE Sepharose FF (Pharmacia Biotech) ion exchange column. The column is equilibrated with 20 mM Piperazine buffer, pH 6.5. The sample is applied to the top of the column and sequentially flushed with 150 mL of 20mM Piperazine buffer, pH 6.5; 150 mL 20 mM Piperazine buffer, pH 6.0; and 150 mL 20 mM Piperazine buffer pH 5.5 with 20 mM NaCl. Size exclusion chromatography is performed on a Sephadex G-75 (Sigma) size exclusion column. The column is equilibrated in 50 mM phosphate buffer, pH 7.0, made from 12.86 mL of 6M NaOH and 27.29 g $KH_2PO_4$, diluted to 4 liters with double distilled water. The sample is applied to the top of the column and the column is flushed with 200 mL of the same 50 mM phosphate buffer of pH 7.0. The enzyme is then characterized using SDS-polyacrylamide gel electrophoresis (SDS-PAGE) and isoelectric focusing. For SDS-PAGE, 10–27% Daichi Sepra-Gels are used under standard Lamelli conditions at each purification step. For isoelectric focusing, pH 3–9 IEF Phastgels are used under standard Pharmicia conditions. SDS polyacrylamide gel electrophoresis (SDS-PAGE) suggests a molecular weight of approximately 40 kDa for the keratinase produced by strain 138B. Isoelectric focusing indicates a pI of 5.5 for this keratinase. The keratinase produced by strain 138B is a serine protease; it exhibits keratinase activity and general proteolytic activity.

The preferred embodiments, examples, and other disclosures in this specification are not to be taken as limiting the present invention. The scope of the invention is defined by the claims and their equivalents.

We claim:

1. A purified keratinase, produced by a bacterial strain of *Bacillus licheniformis* having all of the identifying characteristics of strain O.W.U. 138B, ATCC 55768.

2. An enzymatic composition suitable to enhance the digestibility of feathers in the digestive tract of an animal comprising: (a) an effective amount of a keratinase according to claim 1, and (b) feathers.

3. An enzymatic composition suitable for removing protein-based stains from a fabric selected from the group consisting of wool and silk and without significant damage to the fabric comprising: (a) an effective amount of the keratinase according to claim 1, and (b) a suitable cleaning medium.

4. A purified keratinase, produced by a bacterial strain of *Bacillus licheniformis* having all of the identifying characteristics of O.W.U. 138B, ATCC 55768; said keratinase having a molecular weight of about 40 kDa as measured by SDS polyacrylamide gel and a pI of about 5.5 as measured by isoelectric focusing.

* * * * *